United States Patent [19]

Kanabrocki

[11] Patent Number: 4,781,198

[45] Date of Patent: Nov. 1, 1988

[54] BIOPSY TRACER NEEDLE

[76] Inventor: Eugene L. Kanabrocki, 151 Braddock Dr., Melrose Park, Ill. 60160

[21] Appl. No.: 904,976

[22] Filed: Sep. 8, 1986

[51] Int. Cl.[4] .............................................. A61B 6/00
[52] U.S. Cl. .................................... 128/654; 128/749; 604/21
[58] Field of Search ................ 128/1.1, 654, 656, 653, 128/751, 207.14, 657, 658, 753, 754, 751, 749, 1.2; 604/272, 21, 116

[56] References Cited

U.S. PATENT DOCUMENTS

| 4,096,862 | 6/1978 | DeLuca | 128/656 |
| 4,190,461 | 2/1980 | Hedger | 128/1.2 |
| 4,249,541 | 2/1981 | Pratt | 128/753 |
| 4,606,354 | 8/1986 | Jacob | 128/1.1 |

Primary Examiner—Edward M. Coven
Assistant Examiner—J. P. Lacyk
Attorney, Agent, or Firm—Emrich & Dithmar

[57] ABSTRACT

A method and apparatus for obtaining a sample of tissue from a human comprising, providing a source of gamma radiation in the tissue to be sampled, providing a biopsy tracer needle of a pharmaceutically acceptable metal having a radioactive material selected from the class consisting of Co-57, Cr-S1, Au-195, Cu-64, Zn-65, Fe-55, Ni-63, and Mn-54 in an amount sufficient to be discernible from the radiation emitted from the tissue to be sampled. The position of the biopsy tracer needle with respect to tissue to be sampled is visibly displayed to allow precise location of the biopsy tracer needle in the tissue to be sampled.

7 Claims, 1 Drawing Sheet

BIOPSY TRACER NEEDLE

BACKGROUND OF THE INVENTION

This invention relates to radiological imaging systems, and more particularly a method and apparatus for utilizing of such systems to track and control the location of needle probes within the body. These radiological imaging systems are used so that probes which are inserted into or through body tissue and maneuvered therein are illustrated on a scintigraphic viewing system to disclose the position of the probe in the organ or other tissue within which the probe is to be positioned. An example of the procedures which are used with the method and apparatus of the present invention is in aspiration biopsy In aspiration biopsy, a small hollow needle is inserted directly into the body to the desired tissue or organ, whereupon a tissue sample is withdrawn, such as by vacuum aspiration. The needle is then withdrawn, but because of its relatively insignificant diameter, wound closure occurs normally by muscular and tissue tension, generally without the need for sutures, cauterization or the like. For optimal effectiveness, aspiration biopsy requires that the tip of the needle by precisely accurately placed in the organ to be sampled. When properly performed, these techniques are safe, effective and minimally traumatic.

Various radiological techniques such as X-ray fluoroscopic techniques have been used for ascertaining or estimating the location of tissue to be treated, sampled or diagnosed, and or aiding in the maneuvering of a given probe to its desired body location. These radiological techniques do not permit the organ as well as the needle to be actually visible and suffer from dimensional and accuracy limitations.

A variety of ultrasound images techniques have been suggested, particularly for in vivo imaging of relatively deep soft body tissue. Various ultrasound systems are disclosed in U.S. Pat. No. 4,407,294 issued Oct. 4, 1983 to Vilkomerson, in U.S. Pat. No. 4,431,006 issued Feb. 14, 1984 to Trimmer et al, and U.S. Pat. No. 4,431,005 issued Feb. 14, 1984 to McCormick. These prior art systems have experienced a certain degree of commercial success and are normally effective for their intended uses, but all suffer from various limitations inherent in the ultrasound process and require special electronics and compact, expensive transducer elements.

SUMMARY OF THE INVENTION

The present invention provides an alternative and superior method and apparatus for locating a biopsy needle in a tumor, lesion or other specific pathology. The method and apparatus of the present invention also permit multiple sampling of the same organ or tumor, thereby providing the diagnostician with a very precise sampling technique, heretofore unavailable Accordingly, it is an object of the present invention to provide a method and apparatus for visibly locating a biopsy needle in the process of sampling a tumor, lesion, organ or the like.

Another object of the present invention is to provide a device suitable for insertion into a human being, comprising a pharmaceutically acceptable metal capable of being inserted into a human, and a gamma emitting radioactive material on the metal sufficient to be detected by gamma ray detecting equipment at a point remote from the location of the metal.

Another object of the present invention is to provide a biopsy tracer needle comprising a stainless steel needle having an outer electrolessly plated layer of a gamma emitting radioactive material sufficient to be detected by gamma ray detecting equipment at a point remote from the needle.

Yet another object of the present invention is to provide a method of obtaining a sample of tissue from a human comprising, providing a source of gamma radiation in the tissue to be sampled, providing a biopsy tracer needle of a pharmaceutically acceptable metal having a radioactive material selected from the class consisting of Co-57, Cr-Sl, Au-195, Cu-64, Zn-65, Fe-55, Ni-63 and Mn-54 in an amount sufficient to be discernible from the radiation emitted from the tissue to be sampled, sensing the position of the biopsy tracer needle with respect to tissue to be sampled, providing a visible display of the biopsy tracer needle and the tissue to be sampled, locating the biopsy tracer needle in the tissue to be sampled, and operating the biopsy needle to obtain a tissue sample.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figure 1:
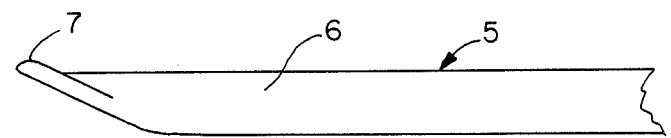
FIG. 1 is a side view of a typical surgical biopsy needle.

Referring now to FIG. 1, there is disclosed a biopsy needle 5 comprising a body portion 6 and a distal end 7 which may be provided with a hole into which tissue is drawn from the organ, lesion, tumor or the like being sampled.

Figure 2:
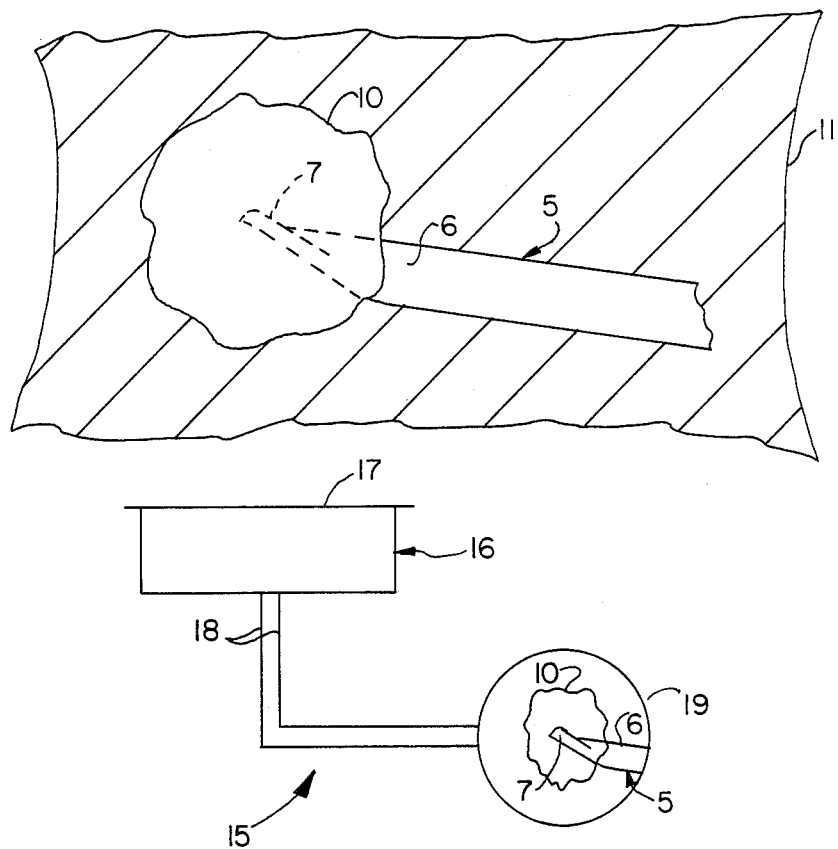
FIG. 2 is a schematic view of a biopsy tracer needle in a tumor, lesion or organ being sample sensed by a suitable scintigraphic device including a display scope.

FIG. 2 shows an organ 10 such as a thyroid in an individual's neck 11 with the biopsy needle 5 being placed with the tip 7 positioned inside the thyroid 10. External to the patient's neck 11 is a scintilation device 15 including a radionuclide sensing head 16 having a radiation detector 17 connected by leads 18 to a scintilation scope 19 which displays on the face thereof the image of the biopsy needle 5 in the thyroid 10. The biopsy needle 5 according to the present invention may be prepared by electrolessly plating a suitable radioactive material onto a stainless steel biopsy needle. The preferred metal plated onto a stainless steel biopsy needle is cobalt; however, chromium, gold, copper, zinc, iron, nickle and manganese are alternative metals. In each case, a radioactive isotope of the metal is used and the radioactive metal is plated onto a small portion of the biopsy needle, preferably about 0.5 centimeters from the end of the needle. For instance, cobalt 57 is the preferred radioisotope used in the invention but chromium 51, gold 195, copper 54, zinc 65, iron 55, nickle 63 and manganese 54 are all alternate materials. The half-like of cobalt 57 is 271 days, thereby providing a device that is useful for at least one year.

A suitable electrolessly plating bath of the present invention is comprised of cobalt 57, present in an amount equal to 1 micro currie (as cobalt chloride) in a 0.15 ml to 0.5 ml of 0.5N HCl solution. the cobalt bath is comprised as follows: An aqueous solution of: 1 volume $_a$+1 volume $_b$+1 volume $_c$ mixture of the following aqueous solutions:

a. $CoSO_4.7 H_2O$ _ _ _ _ _ _ _ _ _ 25.0 gm/dl
  b. NaCl _ _ _ _ _ _ _ _ _ _ _ _ _ 2.0 gm/dl
  c. $H_3BO_3$ (Boric Acid) _ _ _ _ 4.5 gm/dl The stainless steel biopsy needle was prepared in the following manner. In a 10 ml beaker a magnetic stirrer was placed and properly shielded. Into the beaker was placed 0.15 ml of Co-57 with 6.0 ml of Cobalt Bath solution as defined above. Another 10 ml beaker with a Cobalt Bath without any cobalt 57 was also present. A variable 0–30 volt DC power line with a 3 V and 50 mA was provided with sufficient wiring for ("in series electrode connection"). One electrode was the stainless steel biopsy needle and the other electrode was a 20 gauge 9 cm long platinum wire. The adequate shielding was provided by conventional lead bricks. The following procedure was followed:

1. After appropriate "in series" (3 V and 50 mA) connections, clasp the (+) lead to the Pt wire. Clasp the (−) lead to the needle.
2. Lower both electrodes (Pt and the needle), so that approximately 0.5 cm is submerged in the Co-57 Cobalt Bath mixture.
3. Turn "On" the magnetic plate to allow the stirring magnet to rotate freely in the mixture.
4. Simultaneously turn "On" the power supply and the timer. The current voltage should read 3 and the mA 40. Leave the power "ON" for 10 minutes.
5. After 10 minutes turn "Off" the power supply. Raise both electrodes above the Co-57 Cobalt Bath mixture. Remove this "HOT" mixture and shield appropriately.
6. Remove both electrodes (the Pt and the needle), and rinse with copious amounts of tap water. Check the activity of the electroplated needle: typically it will register approximately 11 mR/hr and 16.4±0.2 uCi Co-57.
7. Replace the Pt and the "hot" needle in original positions and immerse to approximately 1.0 cm level in Cobalt Bath solution. Note: This solution is without Co-57.
8. Turn "On" the power supply and the timer and allow to electroplate for 3 minutes.
9. Turn "Off" the power supply. Remove the needle and check its activity: It should read 11 mR/hr.
10. Store this "Tracer Needle" in appropriate shield until use.

In use, the organ, tumor, lesion or the like which is to be sampled is infused with a suitable radionuclide. Typical organs which are subject to this technique are the brain, liver, lung, spleen, kidney, thyroid, bone or the like. After the background radionuclide infusion has taken place, the biopsy tracer needle 5 is inserted into the area and precise imaging can be obtained by use of conventional scintigraphic devices 15, such as those supplied by the Elscint Company, Inc. sold as Model No. Apex 415 Gamma Camera. The scintigraphic device is standard in the art. By use of the scintigraphic device 15 in combination with the prepared biopsy needle 5, it is seen that a particular tumor, lesion or organ may be sampled in a plurality of sites to provide the diagnostician with a clear understanding of the biopsy site and the clear placement of the biopsy needle in relation thereto. The scope of the application of the present invention is very broad and is limited only by gamma ray detectability and background to tissue ratio.

Although the procedure disclosed in the present invention shows a stainless steel biopsy needle having a radioactive cobalt 57 isotope plated on the distal 0.5 cm tip overplated with a non-radioactive cobalt, it is believed that the overplating of non-radioactive cobalt is not necessary but was done to ensure that none of the radioactive cobalt could possibly be left in the patient. It will be appreciated that various other metals with radioactive isotopes as hereinbefore mentioned are useful in the present invention and may be substituted for the cobalt-57 preferred.

The various half lives of the radioisotopes are of consideration of their use.

While there has been described what at present is considered to be the preferred embodiment of the present invention, it will be appreciated that various modifications and alterations may be made therein without departing from the true spirit and scope of the present invention which is intended to be covered in the claims appended hereto.

I claim:

1. A biopsy tracer needle comprising a stainless steel needle having an electrolessly plated layer of a gamma emitting radioactive material sufficient to be detected by gamma ray detecting equipment at a point remote from said needle only on the end of said needle and a non-radioactive material covering the radioactive material.

2. The needle of claim 1, wherein said gamma emitting radioactive material is selected from the class consisting of Co-57, Cr-51, Au-195, Cu-64, Zn-65, Fe-55, Ni-63 and Mn-54.

3. The needle of claim 1, wherein said non-radioactive material is an isotope of the radioactive material.

4. A method of obtaining a sample of tissue from a human comprising, providing a source of gamma radiation in the tissue to be sampled, providing a biopsy tracer needle of a pharmaceutically acceptable metal having a radioactive material selected from the class consisting of Co-57, Cr-S1, Au-195, Cu-64, Zn-65, Fe-55, Ni-63 and Mn-54 in an amount sufficient to be discernible from the radiation emitted from the tissue to be sampled, sensing the position of the biopsy tracer needle with respect to tissue to be sampled, providing a visible display of the biopsy tracer needle and the tissue to be sampled, locating the biopsy tracer needle in the tissue to be sampled, and operating the biopsy needle to obtain a tissue sample.

5. The method of claim 4, wherein the radioactive material in the biopsy needle is Co-57.

6. The method of claim 5, wherein the radioactive Co-57 is electrolessly plated onto a stainless steel needle.

7. The method of claim 6, and further comprising an electrolessly plated layer of non-radioactive cobalt covering the radioactive Co-57.

* * * * *